(12) United States Patent
Biadatti et al.

(10) Patent No.: US 7,767,650 B2
(45) Date of Patent: Aug. 3, 2010

(54) LIGAND ACTIVATORS OF THE RAR RECEPTORS AND PHARMACEUTICAL/COSMETIC APPLICATIONS THEREOF

(75) Inventors: Thibaud Biadatti, Opio (FR); Jean-Marie Arlabosse, Cagnes sur Mer (FR)

(73) Assignee: Galderma Research & Development, Biot (FR)

( * ) Notice: Subject to any disclaimer, the term of this patent is extended or adjusted under 35 U.S.C. 154(b) by 689 days.

(21) Appl. No.: 11/448,830
(22) Filed: Jun. 8, 2006
(65) Prior Publication Data

US 2007/0117761 A1 May 24, 2007

Related U.S. Application Data

(63) Continuation of application No. PCT/EP2004/014809, filed on Dec. 7, 2004.
(60) Provisional application No. 60/529,986, filed on Dec. 17, 2003.

(30) Foreign Application Priority Data

Dec. 8, 2003 (FR) .................... 03 14336

(51) Int. Cl.
| | |
|---|---|
| A61K 31/70 | (2006.01) |
| A61K 31/22 | (2006.01) |
| A61K 31/165 | (2006.01) |
| C07C 69/76 | (2006.01) |
| C07C 59/74 | (2006.01) |
| C07C 65/00 | (2006.01) |
| C07C 65/01 | (2006.01) |

(52) U.S. Cl. .......... 514/23; 514/546; 514/621; 560/51; 560/55; 562/459; 562/473; 562/475
(58) Field of Classification Search .......... 514/354, 514/23, 546, 621; 560/51, 55; 562/459, 562/473, 475

See application file for complete search history.

(56) References Cited

U.S. PATENT DOCUMENTS 5,716,624 A 2/1998 Bernardon 6,046,220 A * 4/2000 Bernardon ............... 514/354

* cited by examiner

Primary Examiner—Taylor Victor Oh
(74) Attorney, Agent, or Firm—Buchanan Ingersoll & Rooney PC

(57) ABSTRACT

Novel ligand compounds having the structural formula (I):

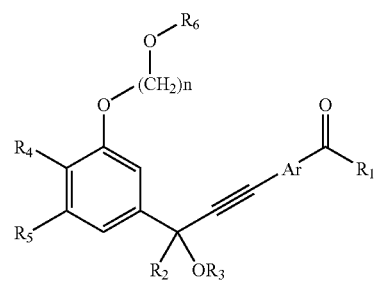

in which:

Ar is a radical selected from among the radicals of formulae (a)-(c) below:

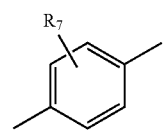

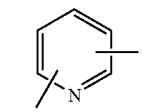

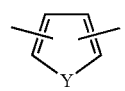

are formulated into pharmaceutical compositions suited for administration in human or veterinary medicine, or, alternatively into cosmetic compositions.

18 Claims, 1 Drawing Sheet

LIGAND ACTIVATORS OF THE RAR RECEPTORS AND PHARMACEUTICAL/COSMETIC APPLICATIONS THEREOF

CROSS-REFERENCE TO PRIORITY/PCT/PROVISIONAL APPLICATIONS

This application claims priority under 35 U.S.C. §119 of FR 03/14336, filed Dec. 8, 2003, and of Provisional Application No. 60/529,986, filed Dec. 17, 2003, and is a continuation of PCT/EP 2004/014809 filed Dec. 7, 2004 and designating the United States, published in the English language as WO 2005/056510 A2 on Jun. 23, 2005, each hereby expressly incorporated by reference and each assigned to the assignee hereof.

BACKGROUND OF THE INVENTION

1. Technical Field of the Invention

The present invention relates to novel compounds that are useful industrial products, which compounds are ligands that are activators of the RAR receptors. This invention also relates to compositions containing said novel ligands and to their formulation into pharmaceutical compositions for administration in human or veterinary medicine, or, alternatively into cosmetic compositions and to the non-therapeutic use of these compositions.

2. Description of Background and/or Related and/or Prior Art

Compounds with activity of retinoid type (vitamin A and its derivatives) are widely described in the literature as having activity in cell proliferation and differentiation processes. These properties give this class of compounds high potential in the treatment or prevention of numerous pathologies, and more particularly in dermatology and cancer. Many biological effects of retinoids are mediated by modulating the nuclear retinoic acid receptors (RAR).

The RAR receptors activate transcription by binding to DNA sequence elements, known as RAR response elements (RARE), in the form of a heterodimer with the retinoid X receptors (known as RXRs).

Three subtypes of human RARs have been identified and described: RARα, RARβ and RARγ.

Chemical compounds with activating activity on receptors of RAR type are known from the prior art. Especially representative are the aromatic heterocyclic biaryl compounds described in EP-0-816,352 B1, which find applications in the treatment of dermatological, rheumatic, respiratory and ophthalmological complaints, conditions or afflictions and also in the cosmetics field.

EP-0-661,258 describes biaromatic propynyl compounds more particularly containing an alkoxy substituent on the aromatic ring. This alkyl chain limits the solubility of the compounds.

Thus, need continues to exist for compounds with better solubility in water, with physicochemical and pharmacokinetic properties that are more suitable for application as medicinal products or cosmetics for man; this better solubility would also allow greater ease of formulation of the active principle in a composition.

SUMMARY OF THE INVENTION

Novel compounds have now surprisingly and unexpectedly been developed that are retinoic acid receptor-activating ligands, containing an O-substituted hydroxyalkyl radical on the aromatic ring, allowing greater solubility in water, and which find applications in human medicine, especially in dermatology, and in the cosmetics field.

Thus, the present invention features compounds having the general formula (I) below:

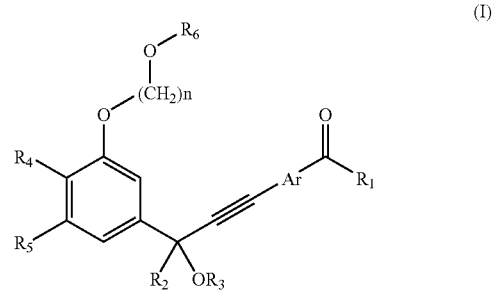

(I)

in which:

Ar is a radical selected from among the radicals of formulae (a)-(c) below:

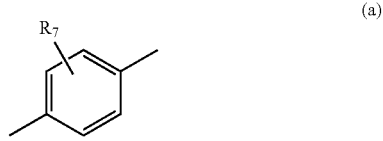
(a)

(b)

(c)

wherein $R_7$ and Y are as defined below;

$R_1$ is:
(a) a hydrogen atom,
(b) an alkyl radical having from 1 to 6 carbon atoms,
(c) a radical of formula:

(d) a radical —$OR_8$,
wherein R, R" and $R_8$ are as defined below;

$R_2$ is a hydrogen atom or an alkyl radical having from 1 to 6 carbon atoms;

$R_3$ is a hydrogen atom, an alkyl radical having from 1 to 6 carbon atoms or a radical —CO—$R_9$,
wherein $R_9$ is as defined below;

$R_4$ and $R_5$ together form, with the adjacent aromatic ring from which they depend, a 5- or 6-membered ring optionally substituted with methyl groups and/or optionally interrupted with an oxygen or sulfur atom;

$R_6$ is an alkyl radical having from 1 to 6 carbon atoms or a radical (CO)$R_{10}$,
wherein $R_{10}$ is as defined below;

$R_7$ is a hydrogen atom, a halogen atom, an alkyl radical having from 1 to 6 carbon atoms or a radical —$OR_{11}$,
wherein $R_{11}$ is as defined below;

$R_8$ is a hydrogen atom, a linear or branched alkyl radical having from 1 to 20 carbon atoms, an alkenyl radical, a monoor polyhydroxyalkyl radical, an optionally substituted aryl or aralkyl radical or a sugar residue or an amino acid or peptide residue;

$R_9$ and $R_{10}$ are each $CF_3$ or an alkyl radical having from 1 to 6 carbon atoms;

$R_{11}$ is H, an alkyl radical having from 1 to 6 carbon atoms or a radical (CO)—$R_{12}$, wherein $R_{12}$ is as defined below;

$R_{12}$ is an alkyl radical having from 1 to 6 carbon atoms;

R' and R" are each a hydrogen atom, an alkyl radical having from 1 to 6 carbon atoms, a mono- or polyhydroxyalkyl radical, an optionally substituted aryl radical or an amino acid, peptide or sugar residue, or alternatively, taken together, form a heterocycle;

Y is an oxygen or sulfur atom;

n is an integer ranging from 2 to 6;

and the salts of the compounds of formula (I) when $R_1$ is an OH function, and also the optical and geometrical isomers of the said compounds of formula (I).

When the compounds according to the invention are in the form of a salt, it is preferably an alkali metal or alkaline-earth metal salt, or, alternatively, a zinc salt or a salt of an organic amine.

BRIEF DESCRIPTION OF THE DRAWING

The FIGURE of Drawing illustrates certain reaction schemes for preparing the compounds of formula (I).

DETAILED DESCRIPTION OF BEST MODE AND SPECIFIC/PREFERRED EMBODIMENTS OF THE INVENTION

Figure 1:
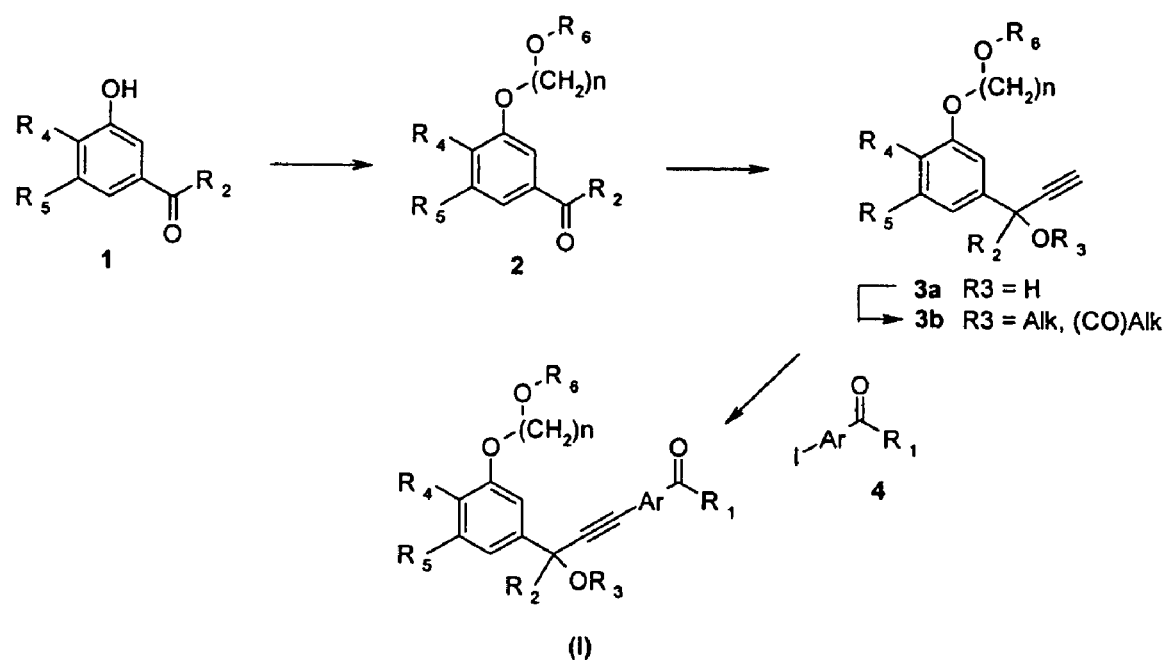

According to the present invention, the term "alkyl having from 1 to 6 carbon atoms" preferably means methyl, ethyl, n-propyl, isopropyl, cyclopropyl, n-butyl, i-butyl, t-butyl, n-pentyl or n-hexyl radicals.

The term "linear or branched alkyl having from 1 to 20 carbon atoms" especially means methyl, ethyl, n-propyl, isopropyl, cyclopropyl, n-butyl, i-butyl, t-butyl, n-pentyl, n-hexyl, 2-ethylhexyl, octyl, dodecyl, hexadecyl or octadecyl radicals.

The term "monohydroxyalkyl radical" means a radical preferably containing 2 or 3 carbon atoms, especially a 2-hydroxyethyl, 2-hydroxypropyl or 3-hydroxypropyl radical.

The term "polyhydroxyalkyl radical" means a radical preferably having from 3 to 6 carbon atoms and from 2 to 5 hydroxyl groups, such as 2,3-dihydroxypropyl, 2,3,4-trihydroxybutyl or 2,3,4,5-tetrahydroxypentyl radicals or a pentaerythritol residue.

The term "aryl radical" preferably means a phenyl radical optionally substituted with at least one halogen, a hydroxyl or a nitro function.

The term "aralkyl radical" preferably means a benzyl or phenethyl radical optionally substituted with at least one halogen, a hydroxyl or a nitro function.

The term "alkenyl radical" means a radical preferably having from 1 to 5 carbon atoms and containing one or more ethylenic unsaturations, more particularly such as an allyl radical.

The term "sugar residue" means a residue derived especially from glucose, galactose or mannose, or alternatively from glucuronic acid, such as 6'-mannosyl, 6'-glucosyl or 6'-galactosyl.

The term "amino acid residue" especially means a residue derived from lysine, glycine or aspartic acid, and the term "peptide residue" more particularly means a dipeptide or tripeptide residue resulting from the combination of amino acids.

The term "heterocycle" preferably means a piperidino, morpholino, pyrrolidino or piperazino radical, optionally substituted in position 4 with a $C_1$-$C_6$ alkyl radical or a mono- or polyhydroxyalkyl radical as defined above.

The term "halogen atom" preferably means a fluorine, chlorine or bromine atom.

According to the present invention, the compounds of formula (I) that are more particularly preferred are those for which at least one, and preferably all, of the conditions below are met:

Ar is the radical (a), n is 2 or 3, $R_2$ is a hydrogen atom, $R_4$ and $R_5$ form, with the adjacent aromatic ring, a 6-membered ring, $R_6$ is an alkyl radical.

Among the compounds of formula (I) according to the present invention, especially representative are the following compounds:

1. 4-{3-Hydroxy-3-[4-(2-methoxyethoxy)-5,5,8,8-tetramethyl-5,6,7,8-tetrahydronaphth-2-yl]prop-1-ynyl}benzoic acid;

2. 4-{3-Hydroxy-3-[4-(2-ethoxyethoxy)-5,5,8,8-tetramethyl-5,6,7,8-tetrahydronaphth-2-yl]prop-1-ynyl}benzoic acid;

3. 4-{3-Hydroxy-3-[4-(2-ethoxyethoxy)-5,5,8,8-tetramethyl-5,6,7,8-tetrahydronaphth-2-yl]prop-1-ynyl}-2-hydroxybenzoic acid;

4. 4-{3-Hydroxy-3-[4-(2-ethoxyethoxy)-5,5,8,8-tetramethyl-5,6,7,8-tetrahydronaphth-2-yl]prop-1-ynyl}benzoic (S)-acid;

5. 4-{3-Hydroxy-3-[4-(2-ethoxyethoxy)-5,5,8,8-tetramethyl-5,6,7,8-tetrahydronaphth-2-yl]prop-1-ynyl}benzoic (R)-acid;

6. 6-{3-Hydroxy-3-[4-(2-ethoxyethoxy)-5,5,8,8-tetramethyl-5,6,7,8-tetrahydronaphth-2-yl]prop-1-ynyl}nicotinic acid;

7. 5-{3-Hydroxy-3-[4-(2-ethoxyethoxy)-5,5,8,8-tetramethyl-5,6,7,8-tetrahydronaphth-2-yl]prop-1-ynyl}pyridine-2-carboxylic acid;

8. 5-{3-[4-(2-Ethoxyethoxy)-5,5,8,8-tetramethyl-5,6,7,8-tetrahydronaphth-2-yl]-3-hydroxyprop-1-ynyl}thiophene-2-carboxylic acid;

9. 4-{3-[4-(2-Ethoxyethoxy)-5,5,8,8-tetramethyl-5,6,7,8-tetrahydronaphth-2-yl]-3-hydroxyprop-1-ynyl}thiophene-2-carboxylic acid;

10. 5-{3-[4-(2-Ethoxyethoxy)-5,5,8,8-tetramethyl-5,6,7,8-tetrahydronaphth-2-yl]-3-hydroxyprop-1-ynyl}thiophene-3-carboxylic acid;

11. 5-{3-[4-(2-Ethoxyethoxy)-5,5,8,8-tetramethyl-5,6,7,8-tetrahydronaphth-2-yl]-3-hydroxyprop-1-ynyl}furan-2-carboxylic acid;

12. 4-{3-[4-(3-Ethoxyethoxy)-5,5,8,8-tetramethyl-5,6,7,8-tetrahydronaphth-2-yl]-3-hydroxyprop-1-ynyl}benzoic acid;

13. 4-{3-[4-(3-Methoxypropoxy)-5,5,8,8-tetramethyl-5,6,7,8-tetrahydronaphth-2-yl]-3-hydroxyprop-1-ynyl}benzoic acid;

14. 4-{3-[4-(4-Methoxybutoxy)-5,5,8,8-tetramethyl-5,6,7,8-tetrahydronaphth-2-yl]-3-hydroxyprop-1-ynyl}benzoic acid;

15. 4-{3-[4-(5-Methoxypentoxy)-5,5,8,8-tetramethyl-5,6,7,8-tetrahydronaphth-2-yl]-3-hydroxyprop-1-ynyl}benzoic acid;

16. 4-{3-[4-(6-Methoxyhexyloxy)-5,5,8,8-tetramethyl-5,6,7,8-tetrahydronaphth-2-yl]-3-hydroxyprop-1-ynyl}benzoic acid;

17. 4-{3-[4-(2-Ethoxyethoxy)-5,5,8,8-tetramethyl-5,6,7,8-tetrahydronaphth-2-yl]-3-hydroxybut-1-ynyl}benzoic acid;

18. 4-{3-[4-(2-Ethoxyethoxy)-5,5,8,8-tetramethyl-5,6,7,8-tetrahydronaphth-2-yl]-3-hydroxypent-1-ynyl}benzoic acid;

19. 4-{3-[4-(2-Ethoxyethoxy)-5,5,8,8-tetramethyl-5,6,7,8-tetrahydronaphth-2-yl]-3-acetoxyprop-1-ynyl}benzoic acid;

20. 4-{3-[4-(2-Ethoxyethoxy)-5,5,8,8-tetramethyl-5,6,7,8-tetrahydronaphth-2-yl]-3-propionyloxyprop-1-ynyl}benzoic acid;

21. 4-{3-[7-(2-Ethoxyethoxy)-1,1,3,3-tetramethyl-1,3-dihydroisobenzofuran-5-yl]-3-hydroxyprop-1-ynyl}benzoic acid;

22. 4-{3-[8-(2-Ethoxyethoxy)-4,4-dimethylchroman-6-yl]-3-hydroxyprop-1-ynyl}benzoic acid;

23. 4-{3-[8-(2-Ethoxyethoxy)-4,4-dimethylthiochroman-6-yl]-3-hydroxyprop-1-ynyl}benzoic acid;

24. 4-{3-[5-(2-Ethoxyethoxy)-4,4-dimethylchroman-7-yl]-3-hydroxyprop-1-ynyl}benzoic acid;

25. 4-{3-[5-(2-Ethoxyethoxy)-4,4-dimethylthiochroman-7-yl]-3-hydroxyprop-1-ynyl}benzoic acid;

26. 4-{3-[4-(2-Acetoxyethoxy)-5,5,8,8-tetramethyl-5,6,7,8-tetrahydronaphth-2-yl]-3-hydroxyprop-1-ynyl}benzoic acid;

27. 4-(3-Hydroxy-3-{5,5,8,8-tetramethyl-4-[2-(2,2,2-trifluoroacetoxy)ethoxy]-5,6,7,8-tetrahydronaphth-2-yl}prop-1-ynyl)benzoic acid;

28. 4-(3-Hydroxy-3-[5,5,8,8-tetramethyl-4-(2-propionyloxyethoxy)-5,6,7,8-tetrahydronaphth-2-yl]prop-1-ynyl}benzoic acid;

29. 4-{3-[4-(2-Ethoxyethoxy)-5,5,8,8-tetramethyl-5,6,7,8-tetrahydronaphth-2-yl]-3-hydroxyprop-1-ynyl}-2-methylbenzoic acid;

30. 2-Chloro-4-{3-[4-(2-ethoxyethoxy)-5,5,8,8-tetramethyl-5,6,7,8-tetrahydronaphth-2-yl]-3-hydroxyprop-1-ynyl}benzoic acid;

31. 4-{3-[4-(2-Ethoxyethoxy)-5,5,8,8-tetramethyl-5,6,7,8-tetrahydronaphth-2-yl]-3-hydroxyprop-1-ynyl}-2-fluorobenzoic acid;

32. 4-{3-[4-(2-Ethoxyethoxy)-5,5,8,8-tetramethyl-5,6,7,8-tetrahydronaphth-2-yl]-3-hydroxyprop-1-ynyl}-3-fluorobenzoic acid;

33. 4-{3-[4-(2-Ethoxyethoxy)-5,5,8,8-tetramethyl-5,6,7,8-tetrahydronaphth-2-yl]-3-hydroxyprop-1-ynyl}-3-methylbenzoic acid;

34. Ethyl 4-{3-[4-(2-ethoxyethoxy)-5,5,8,8-tetramethyl-5,6,7,8-tetrahydronaphth-2-yl]-3-hydroxyprop-1-ynyl}benzoate;

35. Isopropyl 4-{3-[4-(2-ethoxyethoxy)-5,5,8,8-tetramethyl-5,6,7,8-tetrahydronaphth-2-yl]-3-hydroxyprop-1-ynyl}benzoate;

36. Isobutyl 4-{3-[4-(2-ethoxyethoxy)-5,5,8,8-tetramethyl-5,6,7,8-tetrahydronaphth-2-yl]-3-hydroxyprop-1-ynyl}benzoate;

37. 2,3-Dihydroxypropyl 4-{3-[4-(2-ethoxyethoxy)-5,5,8,8-tetramethyl-5,6,7,8-tetrahydronaphth-2-yl]-3-hydroxyprop-1-ynyl}benzoate;

38. 6-Glucosyl 4-{3-[4-(2-ethoxyethoxy)-5,5,8,8-tetramethyl-5,6,7,8-tetrahydronaphth-2-yl]-3-hydroxyprop-1-ynyl}benzoate;

39. 6-Galactosyl 4-{3-[4-(2-ethoxyethoxy)-5,5,8,8-tetramethyl-5,6,7,8-tetrahydronaphth-2-yl]-3-hydroxyprop-1-ynyl}benzoate;

40. 4-{3-[4-(2-Ethoxyethoxy)-5,5,8,8-tetramethyl-5,6,7,8-tetrahydronaphth-2-yl]-3-hydroxyprop-1-ynyl}-N,N-dimethylbenzamide;

41. 4-{3-[4-(2-Ethoxyethoxy)-5,5,8,8-tetramethyl-5,6,7,8-tetrahydronaphth-2-yl]-3-hydroxyprop-1-ynyl}-N,N-diethylbenzamide;

42. (4-{3-[4-(2-Ethoxyethoxy)-5,5,8,8-tetramethyl-5,6,7,8-tetrahydronaphth-2-yl]-3-hydroxyprop-1-ynyl}phenyl)piperidin-1-ylmethanone;

43. (4-{3-[4-(2-Ethoxyethoxy)-5,5,8,8-tetramethyl-5,6,7,8-tetrahydronaphth-2-yl]-3-hydroxyprop-1-ynyl}phenyl)morpholin-4-ylmethanone;

44. (4-{3-[4-(2-Ethoxyethoxy)-5,5,8,8-tetramethyl-5,6,7,8-tetrahydronaphth-2-yl]-3-hydroxyprop-1-ynyl}phenyl)pyrrolidin-1-ylmethanone;

45. (4-{3-[4-(2-Ethoxyethoxy)-5,5,8,8-tetramethyl-5,6,7,8-tetrahydronaphth-2-yl]-3-hydroxyprop-1-ynyl}-N-ethylbenzamide;

46. (4-{3-[4-(2-Ethoxyethoxy)-5,5,8,8-tetramethyl-5,6,7,8-tetrahydronaphth-2-yl]-3-hydroxyprop-1-ynyl}benzoylamino)acetic acid; and 47. 2-(4-{3-[4-(2-Ethoxyethoxy)-5,5,8,8-tetramethyl-5,6,7,8-tetrahydronaphth-2-yl]-3-hydroxyprop-1-ynyl}benzoylamino)-3-phenylpropionic acid.

The present invention also features the processes for preparing the compounds of formula (I), in particular according to the reactions schemes shown in the FIGURE of Drawing.

The compounds of formula (I) may be obtained from starting materials of general formula 1. Specifically, the intermediate of general formula 2 may be obtained after alkylation of the phenoxide derived from the compounds 1 in the presence, for example, of sodium hydride, with a corresponding alkylating group. The propargyl alcohol function of 3a may be obtained by reaction with an ethynyl anion, for example in the presence of ethynylmagnesium bromide. The compounds of general formula 3b may be obtained by simple alkylation or acylation reaction, for example by reaction with an alkyl iodide in the presence of silver oxide or an acyl chloride in basic medium, respectively. The compounds of general formula (I) are then obtained by coupling the compounds of formula 3 with a corresponding aryl iodide 4, for example under the Sonogashira coupling conditions.

The compounds according to the invention have activating properties of RAR-type receptors. This RAR-receptor activating activity is measured in a test of transactivation by means of the dissociation constant Kdapp (apparent) and the $AC_{50}$ (concentration that gives 50% of the reference molecule activity).

According to the invention, the expression "activator of RAR-type receptors" means any compound which, for at least one of the RAR subtypes, has a dissociation constant Kdapp and an $AC_{50}$ value of less than or equal to 1 µm, in a transactivation test as described in Example 6.

The preferred compounds of the present invention have, for at least one of the RAR subtypes, a dissociation constant Kdapp of less than or equal to 500 nM and advantageously less than or equal to 100 Nm, and an $AC_{50} \leq 100$ nM.

The present invention also features the compounds of formula (I) as described above, as medicinal products.

The compounds according to the invention are particularly suitable in the following fields of treatment:

for treating dermatological complaints, conditions or afflictions associated with a keratinization disorder relating to cell differentiation and proliferation, especially for treating common acne, comedones, polymorphs, acne rosacea, nodulocystic acne, acne conglobata, senile acne, and secondary acnes such as solar acne, medication-related acne or occupational acne;

for treating other types of keratinization disorders, especially ichthyosis, ichthyosiform conditions, Darier's disease, palmoplantar keratoderma, leukoplakia and leukoplakiform conditions, and cutaneous or mucous (buccal) lichen;

for treating other dermatological complaints, conditions or afflictions with an inflammatory immunoallergic component, with or without cell proliferation disorder, and especially all forms of psoriasis, whether cutaneous, mucous or ungual, and even psoriatic rheumatism, or cutaneous atopy, such as eczema, or respiratory atopy, or alternatively gingival hypertrophy;

for treating all dermal or epidermal proliferations, whether benign or malignant, and whether of viral origin or otherwise, such as common warts, flat warts and verruciform epidermodysplasia, oral or florid papillomatoses, T lymphoma, and proliferations that may be induced by ultraviolet radiation, especially in the case of basocellular and spinocellular epithelioma, and also any cutaneous precancerous lesion such as keratoacanthomas;

for treating other dermatological disorders such as immune dermatoses, such as lupus erythematosus, immune bullous diseases and collagen diseases, such as scleroderma;

in the treatment of dermatological or general complaints, conditions or afflictions having an immunological component;

for treating certain ophthalmological disorders, especially corneopathies, for preventing or curing the stigmata of epidermal and/or dermal atrophy induced by local or systemic corticosteroids, or any other form of cutaneous atropy, in the treatment of any cutaneous or general complaint, condition or affliction of viral origin, in the treatment of skin disorders caused by exposure to UV radiation, and also for repairing or combating aging of the skin, whether photoinduced or chronological aging, or for reducing pigmentations and actinic keratosis, or any pathology associated with chronological or actinic aging, such as xerosis;

for combating sebaceous function disorders, such as the hyperseborrhoea of acne or simple seborrhoea;

for preventing or treating cicatrization disorders, or for preventing or repairing stretch marks, or alternatively for promoting cicatrization;

in the treatment of pigmentation disorders, such as hyperpigmentation, melasma, hypopigmentation or vitiligo;

in the treatment of lipid metabolism complaints, conditions or afflictions such as obesity, hyperlipidaemia, or non-insulin-dependent diabetes;

in the treatment of inflammatory complaints, conditions or afflictions such as arthritis;

in the treatment or prevention of cancerous or precancerous conditions;

in the prevention or treatment of alopecia of various origins, especially alopecia caused by chemotherapy or radiation;

in the treatment of disorders of the immune system, such as asthma, type I sugar diabetes, multiple sclerosis or other selective dysfunctions of the immune system; and in the treatment of complaints, conditions or afflictions of the cardiovascular system, such as arteriosclerosis or hypertension.

This invention also features pharmaceutical compositions comprising, formulated into a physiologically acceptable medium, at least one compound of formula (I) as defined above.

The present invention also features novel medicinal compositions suited especially for treating the abovementioned maladies, which comprise, formulated into a pharmaceutically acceptable support that is compatible with the mode of administration selected for this composition, at least one compound of formula (I), an optical isomer or a salt thereof.

The compositions according to the invention may be administered orally, enterally, parenterally, topically or ocularly. The pharmaceutical composition is preferably packaged in a form that is suitable for topical application.

Via the oral route, the composition may be in the form of tablets, gel capsules, dragees, syrups, suspensions, solutions, powders, granules, emulsions, suspensions of microspheres or nanospheres or lipid or polymer vesicles allowing a controlled release. Via the parenteral route, the composition may be in the form of solutions or suspensions for infusion or for injection.

The compounds according to the invention are generally administered in a regime or regimen at a daily dose of about 0.01 mg/kg to 100 mg/kg of body weight, in 1 to 3 dosage intakes.

The compounds are administered systemically, at a concentration generally of from 0.001% to 10% by weight and preferably from 0.01% to 1% by weight relative to the weight of the composition.

Via the topical route, the pharmaceutical composition according to the invention is more particularly suited for treating the skin and mucous membranes and may be in liquid, pasty or solid form, and more particularly in the form of ointments, creams, milks, pomades, powders, impregnated pads, syndets, solutions, gels, sprays, mousses, suspensions, sticks, shampoos or washing bases. It may also be in the form of suspensions of microspheres or nanospheres or of lipid or polymer vesicles or gelled or polymer patches allowing a controlled release.

The compounds are administered topically at a concentration generally of from 0.001% to 10% by weight and preferably from 0.01% to 1% by weight, relative to the total weight of the composition.

The compounds of formula (I) according to the invention also find application in cosmetics, in particular in body and hair hygiene and especially for treating acne-prone skin, for promoting regrowth of the hair or for limiting hair loss, for combating the greasy appearance of the skin or the hair, in protection against the harmful aspects of sunlight or in the treatment of physiologically dry skin, and for preventing and/or combating photoinduced or chronological aging.

The present invention thus also features cosmetic compositions comprising, formulated into a physiologically acceptable support, at least one of the compounds of formula (I).

The invention also features the non-therapeutic use of a cosmetic composition comprising at least one compound of formula (I) for preventing and/or treating the signs of aging and/or dry skin.

This invention also features the non-therapeutic use of a cosmetic composition comprising at least one compound of formula (I) for body or hair hygiene.

The cosmetic compositions according to the invention containing, in a physiologically acceptable medium, at least one compound of formula (I) or an optical or geometrical isomer thereof or a salt thereof, may be especially in the form of a cream, a milk, a gel, suspensions of microspheres or nanospheres or lipid or polymer vesicles, impregnated pads, solutions, sprays, mousses, sticks, soaps, washing bases or shampoos.

The concentration of compound of formula (I) in the cosmetic composition is preferably from 0.001% to 3% by weight relative to the total weight of the composition.

The term "physiologically acceptable medium" means a medium that is compatible with the skin and possibly with its integuments (eyelashes, nails or hair) and/or mucous membranes.

The pharmaceutical and cosmetic compositions as described above may also contain inert additives, or even pharmacodynamically active additives as regards the pharmaceutical compositions, or combinations of these additives, and especially:

wetting agents;
flavor enhancers;
preservatives such as para-hydroxybenzoic acid esters;
stabilizers;
moisture regulators;
pH regulators;
osmotic pressure modifiers;
emulsifiers;
UV-A and UV-B screening agents;
antioxidants such as α-tocopherol, butylhydroxyanisole, butylhydroxytoluene, superoxide dismutase, ubiquinol or certain metal-chelating agents;
depigmenting agents such as hydroquinone, azelaic acid, caffeic acid or kojic acid;
emollients;
moisturizers, for instance glycerol, PEG 400, thiamorpholinone and its derivatives or urea;
anti-seborrhoeic or anti-acne agents, such as S-carboxymethylcysteine, S-benzylcysteamine, salts thereof or derivatives thereof, or benzoyl peroxide;
antibiotics, for instance erythromycin and its esters, neomycin, clindamycin and its esters, and tetracyclines;
anti-fungal agents such as ketoconazole or poly-4,5-methylene-3-isothiazolidones;
agents for promoting regrowth of the hair, for instance Minoxidil (2,4-diamino-6-piperidinopyrimidine 3-oxide) and its derivatives, Diazoxide (7-chloro 3-methyl-1,2,4-benzothiadiazine 1,1-dioxide) and Phenyloin (5,4-diphenylimidazolidine-2,4-dione);
non-steroidal anti-inflammatory agents;
carotenoids and especially β-carotene;
anti-psoriatic agents such as anthralin and its derivatives;
eicosa-5,8,11,14-tetraynoic acid and eicosa-5,8,11-triynoic acid, and esters and amides thereof;
retinoids, i.e., natural or synthetic RXR receptor ligands;
corticosteroids or oestrogens;
α-hydroxy acids and α-keto acids or derivatives thereof, such as lactic acid, malic acid, citric acid, glycolic acid, mandelic acid, tartaric acid, glyceric acid or ascorbic acid, and also salts, amides or esters thereof, or β-hydroxy acids or derivatives thereof, such as salicylic acid and its salts, amides or esters;
ion-channel blockers such as potassium-channel blockers;
or alternatively, more particularly for pharmaceutical compositions, in combination with medicinal products known to interfere with the immune system (for example cyclosporin, FK 506, glucocorticoids, monoclonal antibodies, cytokines or growth factors, etc.).

Needless to say, one skilled in this art will take care to select the optional compound(s) to be added to these compositions such that the advantageous properties intrinsically associated with the present invention are not, or are not substantially, adversely affected by the envisaged addition.

The present invention also features a cosmetic regime or regimen for enhancing the skin, wherein a composition comprising at least one compound of formula (I) as defined above is topically applied onto the skin.

Activation of the retinoic acid receptors with the compounds of formula (I) according to the invention makes it possible to obtain skin whose surface aspect is enhanced.

Several examples of the production of active compounds of formula (I) according to the invention, biological activity results thereof and also various specific formulations based on such compounds, will now be given, it being understood that same are intended only as illustrative and in nowise limitative. In said examples to follow, all parts and percentages are given by weight, unless otherwise indicated.

EXAMPLES

Example 1

Synthesis of 4-{3-Hydroxy-3-[4-(2-methoxyethoxy)-5,5,8,8-tetramethyl-5,6,7,8-tetrahydronaphth-2-yl] prop-1-ynyl}benzoic acid a. Preparation of 3-Bromo-5,5,8,8-tetramethyl-5,6,7,8-tetrahydronaphth-1-ol 60 g (347 mmol) of 3-bromophenol are dissolved in 600 mL of dichloromethane. This solution is added to a solution of 46 g (347 mmol) of aluminum chloride in 200 mL of dichloromethane. 127 g (694 mmol) of 2,5-dichloro-2,5-dimethylhexane are added in 10 g portions every 40 minutes. The medium is then stirred for 10 hours, after which it is poured onto ice and extracted with dichloromethane. The residue obtained is dissolved in ethyl ether and this organic phase is then washed with 1N sodium hydroxide solution, and then with water. The residue obtained is purified by chromatography (eluent:heptane and then 1/1 heptane/dichloromethane). A thick oil is obtained (67 g; yield=68%).

b. Preparation of 4-Hydroxy-5,5,8,8-tetramethyl-5,6,7,8-tetrahydronaphthalene-2-carbaldehyde 30 g (106 mmol) of 3-bromo-5,5,8,8-tetramethyl-5,6,7,8-tetrahydronaphth-1-ol are dissolved in 500 mL of anhydrous THF. The medium is cooled to −78° C. and 156 mL (265 mmol) of tert-butyllithium are then added dropwise. After 45 minutes at this temperature, 12.3 mL (159 mmol) of dimethylformamide are added. The mixture is warmed to room temperature and then treated with 1N hydrochloric acid solution and extracted with ethyl acetate. The residue obtained is then purified by chromatography (eluent: 9/1 heptane/ethyl acetate). A white solid is obtained (m=16.5 g; yield=67%; m.p.=144° C.).

c. Preparation of 5,5,8,8-Tetramethyl-4-(2-methoxyethoxy)-5,6,7,8-tetrahydronaphthalene-2-carbaldehyde 34 g (148 mmol) of 4-hydroxy-5,5,8,8-tetramethyl-5,6,7,8-tetrahydronaphthalene-2-carbaldehyde are dissolved in 400 mL of anhydrous DMF. 7.2 g (178 mmol) of 60% sodium hydride are then added portionwise, and the reaction medium is stirred for 1 hour. 16.5 mL (178 mmol) of 2-methoxyethyl chloride are added dropwise, and the medium is stirred at room temperature for 2 hours and then hydrolysed and extracted with ethyl ether. The organic phase is washed with 1N sodium hydroxide solution and then three times with water. The residue obtained is purified by chromatography (eluent:heptane). A yellow oil is obtained (m=42.7 g; yield=95%).

d. Preparation of 1-[5,5,8,8-Tetramethyl-4-(2-methoxyethoxy)-5,6,7,8-tetrahydronaphth-2-yl]prop-2-ynyl-1-ol 0.65 g (2.1 mmol) of 5,5,8,8-tetramethyl-4-(2-methoxyethoxy)-5,6,7,8-tetrahydronaphthalene-2-carbaldehyde is dissolved in 20 mL of THF. 6.4 mL (3.2 mmol) of 0.5N ethylmagnesium bromide solution are added and the reaction medium is then stirred for 1 hour. After treatment with 1N hydrochloric acid solution and extraction with ethyl acetate, followed by evaporation, the residue is purified by chromatography on a column of silica (eluent: 8/2 heptane/EtOAC). A yellow oil is obtained (m=0.48 g; yield=69%).

e. Synthesis of 4-{3-Hydroxy-3-[4-(2-methoxyethoxy)-5,5,8,8-tetramethyl-5,6,7,8-tetrahydronaphth-2-yl]prop-1-ynyl}benzoic acid 0.4 g (1.2 mmol) of 1-[5,5,8,8-tetramethyl-4-(2-methoxyethoxy)-5,6,7,8-tetrahydronaphth-2-yl]prop-2-ynyl-1-ol and 210 mg (0.8 mmol) of 4-iodobenzoic acid are dissolved in 5 mL of DMF and 2 mL of triethylamine. 10 mg of copper iodide and 20 mg of dichloropalladiumbis(triphenylphosphine) are added and the reaction medium is stirred at 50° C. for 2 hours 30 minutes. The reaction medium is poured into ammonium chloride solution and extracted with ethyl acetate. The residue is purified on a column of silica (eluent: 6/4 heptane/EtOAC). The desired product is obtained in the form of a yellowish powder (m=290 mg; yield=83%; m.p.=150° C.). $^1$H NMR (DMSO D$_6$): 1.24 (s, 6H); 1.36 (s, 6H); 1.56-1.60 (m, 4H); 3.33 (s, 3H); 3.73 (m, 2H); 4.08 (m, 2H); 5.53 (d, J=4.9 Hz, 1H); 6.10 (d, J=4.8 Hz, 1H); 6.90 (s, 1H); 7.12 (s, 1H); 7.55 (d, J=8.3 Hz, 2H); 7.93 (d, J=8.3 Hz, 2H), 13.1 (bs, 1H).

Example 2

Synthesis of 4-{3-Hydroxy-3-[4-(2-ethoxyethoxy)-5,5,8,8-tetramethyl-5,6,7,8-tetrahydronaphth-2-yl]prop-1-ynyl}benzoic acid a. Preparation of 5,5,8,8-Tetramethyl-4-(2-ethoxyethoxy)-5,6,7,8-tetrahydronaphthalene-2-carbaldehyde 36 g (156 mmol) of 4-hydroxy-5,5,8,8-tetramethyl-5,6,7,8-tetrahydronaphthalene-2-carbaldehyde are dissolved in 400 mL of anhydrous DMF. 6.5 g (163 mmol) of 60% sodium hydride are added portionwise and the reaction medium is stirred for 1 hour. 25 g (163 mmol) of 2-ethoxyethyl bromide are added portionwise and the medium is stirred at room temperature for 2 hours and then hydrolysed and extracted with ethyl ether. The organic phase is washed with 1N sodium hydroxide solution, and then three times with water. The residue obtained is purified by chromatography (eluent:heptane). A yellow oil is obtained (m=40.7 g; yield=86%).

b. Preparation of 1-[5,5,8,8-Tetramethyl-4-(2-ethoxyethoxy)-5,6,7,8-tetrahydronaphth-2-yl]prop-2-yn-1-ol 40 g (131 mmol) of 5,5,8,8-tetramethyl-4-(2-ethoxyethoxy)-5,6,7,8-tetrahydronaphthalene-2-carbaldehyde are dissolved in 400 mL of THF. 290 mL (145 mmol) of 0.5N ethynylmagnesium bromide solution are added and the reaction medium is then stirred for 1 hour. After treatment with 1N hydrochloric acid solution and extraction with ethyl acetate, followed by evaporation, the residue is purified by chromatography on a column of silica (eluent: 8/2 heptane/EtOAC). A yellow oil is obtained (m=42 g; yield=97%).

c. Synthesis of 4-{3-Hydroxy-3-[4-(2-ethoxyethoxy)-5,5,8,8-tetramethyl-5,6,7,8-tetrahydronaphth-2-yl]-prop-1-ynyl}benzoic acid 5.4 g (15 mmol) of 1-[5,5,8,8-tetramethyl-4-(2-ethoxyethoxy)-5,6,7,8-tetrahydronaphth-2-yl]prop-2-yn-1-ol and 2.6 g (11 mmol) of 4-iodobenzoic acid are dissolved in 125 mL of DMF and 50 mL of triethylamine. 110 mg of copper iodide and 210 mg of dichloropalladiumbis(triphenylphosphine) are added, and the reaction medium is stirred at 50° C. for 2 hours 30 minutes. The reaction medium is poured into ammonium chloride solution and extracted with ethyl acetate. The residue is purified on a column of silica (eluent: 6/4 heptane/EtOAc). The desired product is obtained in the form of yellowish crystals (m=2.5 g; yield=50%; m.p.=158° C.) $^1$H NMR (DMSO D$_6$): 1.12 (t, J=7.0 Hz, 3H); 1.23 (s, 6H); 1.35 (s, 6H); 1.56-1.60 (m, 4H); 3.50 (q, J=7.0 Hz, 2H); 3.75 (m, 2H); 4.06 (m, 2H); 5.52 (d, J=5.0 Hz, 1H); 6.09 (d, J=4.9 Hz, 1H); 6.90 (s, 1H); 7.11 (s, 1H); 7.54 (d, J=8.3 Hz, 2H); 7.93 (d, J=8.3 Hz, 2H), 13.1 (bs, 1H).

Example 3

Synthesis of 4-{3-Hydroxy-3-[4-(2-ethoxyethoxy)-5,5,8,8-tetramethyl-5,6,7,8-tetrahydronaphth-2-yl]prop-1-ynyl}-2-hydroxybenzoic acid a. Synthesis of 4-{3-Hydroxy-3-[4-(2-ethoxyethoxy)-5,5,8,8-tetramethyl-5,6,7,8-tetrahydronaphth-2-yl]prop-1-ynyl}-2-hydroxybenzoic acid 200 mg (0.6 mmol) of 1-[5,5,8,8-tetramethyl-4-(2-ethoxyethoxy)-5,6,7,8-tetrahydronaphth-2-yl]prop-2-yn-1-ol (Example 2b) and 175 mg (0.4 mmol) of 2-hydroxy-4-iodobenzoic acid are dissolved in 5 mL of DMF and 2 mL of triethylamine. 10 mg of copper iodide and 20 mg of dichloropalladiumbis(triphenylphosphine) are added, and the reaction medium is stirred at 50° C. for 2 hours 30 minutes. The reaction medium is poured into ammonium chloride solution and extracted with ethyl acetate. The residue is purified on a column of silica (eluent: 5/5 heptane/EtOAc). The desired product is obtained in the form of a yellowish powder (m=80 mg; yield=42%; m.p.=120° C.) $^1$H NMR (DMSO D$_6$): 1.13 (t, J=7.0 Hz, 3H); 1.24 (s, 6H); 1.36 (s, 6H); 1.56-1.61 (m, 4H); 3.52 (q, J=7.0 Hz, 2H); 3.76 (m, 2H); 4.07 (m, 2H); 5.51 (s, 1H); 6.15 (bs, 1H); 6.89 (s, 1H); 6.97 (m, 2H); 7.11 (s, 1H); 7.77-7.79 (m, 1H), 11.5 (bs, 1H).

Example 4

Synthesis of 4-{3-Hydroxy-3-[4-(2-ethoxyethoxy)-5,5,8,8-tetramethyl-5,6,7,8-tetrahydronaphth-2-yl]-prop-1-ynyl}benzoic (S)-acid a. Preparation of (R)-1-[5,5,8,8-Tetramethyl-4-(2-ethoxyethoxy)-5,6,7,8-tetrahydronaphth-2-yl]prop-2-yn-1-ol 36 g (110 mmol) of 1-[5,5,8,8-tetramethyl-4-(2-ethoxyethoxy)-5,6,7,8-tetrahydronaphth-2-yl]prop-2-yn-1-ol (Example 2b) are dissolved in 75 mL of heptane and 10.2 ml of vinyl acetate. 7.26 g of enzyme PS30 are added, and the reaction medium is stirred and heated to 38° C. After 72 hours, the reaction medium is filtered and concentrated under reduced pressure. Two products are separated out by chromatography: 1-[5,5,8,8-tetramethyl-4-(2-ethoxyethoxy)-5,6,7,8-tetrahydronaphth-2-yl]prop-2-yn-1-ol (R)-acetate and (S)-1-[5,5,8,8-tetramethyl-4-(2-ethoxyethoxy)-5,6,7,8-tetrahydronaphth-2-yl]prop-2-yn-1-ol, which will be used for Example 5.18 g (48 mmol) of 1-[5,5,8,8-tetramethyl-4-(2-ethoxyethoxy)-5,6,7,8-tetrahydronaphth-2-yl]prop-2-yn-1-ol (R)-acetate are thus dissolved in 500 mL of a 2% solution of $K_2CO_3$ in methanol and the medium is stirred for 3 hours. The reaction medium is then treated with 0.01N hydrochloric acid solution and extracted with ethyl acetate. The residue obtained is purified by chromatography (eluent: 8/2 heptane/EtOAc). A colorless oil is obtained (m=15 g, yield=41%).

b. Synthesis of 4-{3-Hydroxy-3-[4-(2-ethoxyethoxy)-5,5,8,8-tetramethyl-5,6,7,8-tetrahydronaphth-2-yl]prop-1-ynyl}benzoic (S)-acid In a manner similar to that of Example 2c, by reaction of 12 g (36 mmol) of (R)-1-[5,5,8,8-tetramethyl-4-(2-ethoxyethoxy)-5,6,7,8-tetrahydronaphth-2-yl]prop-2-yn-1-ol, 6.3 g (25 mmol) of 4-iodobenzoic acid in the presence of 275 mg of copper iodide and 500 mg of dichloropalladiumbis(triphenylphosphine). The desired product is obtained in the form of a whitish powder (m=9.4 g; yield=84%; m.p.=96° C.) $^1$H NMR (DMSO $D_6$): 1.12 (t, J=7.0 Hz, 3H); 1.23 (s, 6H); 1.35 (s, 6H); 1.56-1.60 (m, 4H); 3.50 (q, J=7.0 Hz, 2H); 3.75 (m, 2H); 4.06 (m, 2H); 5.52 (d, J=5.0 Hz, 1H); 6.09 (d, J=4.9 Hz, 1H); 6.90 (s, 1H); 7.11 (s, 1H); 7.54 (d, J=8.3 Hz, 2H); 7.93 (d, J=8.3 Hz, 2H), 13.1 (bs, 1H).

Example 5

Synthesis of 4-{3-Hydroxy-3-[4-(2-ethoxyethoxy)-5,5,8,8-tetramethyl-5,6,7,8-tetrahydronaphth-2-yl]prop-1-ynyl}benzoic (R)-acid In a manner similar to that of Example 4b, by reaction of 15 g (45 mmol) of (S)-1-[5,5,8,8-tetramethyl-4-(2-ethoxyethoxy)-5,6,7,8-tetrahydronaphth-2-yl]prop-2-yn-1-ol (obtained in Example 4a), 7.9 g (32 mmol) of 4-iodobenzoic acid in the presence of 350 mg of copper iodide and 630 mg of dichloropalladiumbis(triphenylphosphine). The desired product is obtained in the form of a whitish powder (m=8.7 g; yield=47%; m.p.=94° C.) $^1$H NMR (DMSO $D_6$): 1.12 (t, J=7.0 Hz, 3H); 1.23 (s, 6H); 1.35 (s, 6H); 1.56-1.60 (m, 4H); 3.50 (q, J=7.0 Hz, 2H); 3.75 (m, 2H); 4.06 (m, 2H); 5.52 (d, J=5.0 Hz, 1H); 6.09 (d, J=4.9 Hz, 1H); 6.90 (s, 1H); 7.11 (s, 1H); 7.54 (d, J=8.3 Hz, 2H); 7.93 (d, J=8.3 Hz, 2H), 13.1 (bs, 1H).

Example 6

Transactivation Test

The activation of receptors with an agonist (activator) in HeLa cells leads to the expression of a reporter gene, luciferase, which, in the presence of a substrate, generates light. The activation of the receptors may thus be measured by quantifying the luminescence produced after incubating the cells in the presence of a reference antagonist. The activating products displace the antagonist from its site, thus allowing activation of the receptor. The activity is measured by quantifying the increase in light produced. This measurement makes it possible to determine the activating activity of the compounds according to the invention.

Determination of the Kdapp:

In this study, a constant is determined which is the affinity of the molecule for the receptor. Since this value can fluctuate depending on the basal activity and the expression of the receptor, it is referred to as the Kdapparent (KdApp).

To determine this constant, the cells are brought into contact with a concentration of the test product and a concentration of the reference antagonist, 4-(5,5-dimethyl-8-p-tolyl-5,6-dihydronaphth-2-ylethynyl)benzoic acid. Measurements are also taken for the total agonist (4-[2-(5,5,8,8-tetramethyl-5,6,7,8-tetrahydronaphth-2-yl)propenyl]benzoic acid) and inverse agonist, 4-{(E)-3-[4-(4-tert-butylphenyl)-5,5,8,8-tetramethyl-5,6,7,8-tetrahydro-2-naphthyl]-3-oxopropenyl}benzoic acid, controls.

These crossed curves make it possible to determine the $AC_{50}$ values (concentration at which 50% activation is observed) for the reference ligand at various concentrations of test product. These $AC_{50}$ values are used to calculate the Schild regression by plotting a straight line corresponding to the Schild equation ("quantitation in receptor pharmacology" Terry P. Kenakin, *Receptors and Channels*, 2001, 7, 371-385).

In the case of an agonist, an $AC_{50}$ value (concentration that gives 50% of the activity) is calculated by plotting the curve of the product at the concentration of the reference ligand that gives 80% activation.

The HeLa cell lines used are stable transfectants containing the plasmids ERE-βGlob-Luc-SV-Neo (reporter gene) and RAR (α, β, γ) ER-DBD-puro. These cells are inoculated into 96-well plates at a rate of 10,000 cells per well in 100 µl of DMEM medium without phenol red, and supplemented with 10% defatted calf serum. The plates are then incubated at 37° C. and 7% $CO_2$ for 4 hours.

The various dilutions of the test products, of the reference ligand (4-(5,5-dimethyl-8-p-tolyl-5,6-dihydronaphth-2-yl) ethynyl)benzoic acid, of the 100% control (100 nM 4-[2-(5,5,8,8-tetramethyl-5,6,7,8-tetrahydro-2-naphthyl)propenyl] benzoic acid) and of the 0% control (500 nM 4-{(E)-3-[4-(4-tert-butylphenyl)-5,5,8,8-tetramethyl-5,6,7,8-tetrahydro-2-naphthyl]-3-oxopropenyl}benzoic acid) are added at a rate of 5 µl per well. The plates are then incubated for 18 hours at 37° C. and 7% $CO_2$.

The culture medium is removed by turning over and 100 µl of a 1:1 PBS/luciferine mixture is added to each well. After 5 minutes, the plates are read using the luminescence detector.

|  | RAR alpha | | RAR beta | | RAR gamma | |
| --- | --- | --- | --- | --- | --- | --- |
|  | Kdapp (nM) | $AC_{50}$ (nM) | Kdapp (nM) | $AC_{50}$ (nM) | Kdapp (nM) | $AC_{50}$ (nM) |
| Ex 1 | 60 | 400 | 60 | 45 | 2 | 2 |
| Ex 2 | 1000 | 900 | 250 | 500 | 30 | 50 |
| Ex 3 | 30 | 150 | 120 | 100 | 1 | 1 |
| Ex 4 | 120 | 800 | 250 | 200 | 1 | 1.2 |
| Ex 5 | 120 | 800 | 250 | 200 | 1 | 1.8 |

The results obtained with the compounds according to the invention clearly show Kdapp values≦100 nM and an $AC_{50}$ value≦100 nM for at least one of the receptor subtypes, this clearly demonstrating an increase in the signal, and in the luminescence in the presence of the reference antagonist. The compounds according to the invention are thus clearly activators of retinoic acid receptors (RAR).

Example 7

Formulation Examples

This example illustrates various specific formulations based on the compounds according to the invention.

A—Oral Route:
(a) 0.2 g Tablet:

| | |
|---|---|
| Compound of Example 5 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable Suspension in 5 ml Ampoules:

| | |
|---|---|
| Compound of Example 3 | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavoring | qs |
| Purified water qs | 5 ml |

(c) 0.8 g Tablet:

| | |
|---|---|
| Compound of Example 4 | 0.500 g |
| Pregelatinized starch | 0.100 g |
| Microcrystalline cellulose | 0.115 g |
| Lactose | 0.075 g |
| Magnesium stearate | 0.010 g |

(d) Drinkable Suspension in 10 ml Ampoules:

| | |
|---|---|
| Compound of Example 2 | 0.200 g |
| Glycerol | 1.000 g |
| 70% sorbitol | 1.000 g |
| Sodium saccharinate | 0.010 g |
| Methyl para-hydroxybenzoate | 0.080 g |
| Flavoring | qs |
| Purified water qs | 10 ml |

B—Parenteral Route:
(a) Composition:

| | |
|---|---|
| Compound of Example 3 | 0.002 g |
| Ethyl oleate | qs 10 g |

(b) Composition:

| | |
|---|---|
| Compound of Example 1 | 0.05% |
| Polyethylene glycol | 20% |
| 0.9% NaCl solution | qs 100 |

(c) Composition:

| | |
|---|---|
| Compound of Example 3 | 2.5% |
| Polyethylene glycol 400 | 20% |
| 0.9% NaCl solution | qs 100 |

(d) Injectable Cyclodextrin Composition:

| | |
|---|---|
| Compound of Example 3 | 0.1 mg |
| β-Cyclodextrin | 0.10 g |
| Water for injection | qs 10.00 g |

C—Topical Route:
(a) Ointment:

| | |
|---|---|
| Compound of Example 2 | 0.020 g |
| Isopropyl myristate | 81.700 g |
| Liquid petroleum jelly fluid | 9.100 g |
| Silica ("Aerosil 200" marketed by Degussa) | 9.180 g |

(b) Ointment:

| | |
|---|---|
| Compound of Example 5 | 0.300 g |
| White petroleum jelly codex qs | 100 g |

(c) Nonionic Water-in-oil Cream:

| | |
|---|---|
| Compound of Example 4 | 0.100 g |
| Mixture of emulsifying lanolin alcohols, waxes and oils ("Anhydrous Eucerin" marketed by BDF) | 39.900 g |
| Methyl para-hydroxybenzoate | 0.075 g |
| Propyl para-hydroxybenzoate | 0.075 g |
| Sterile demineralized water qs | 100 g |

(d) Lotion:

| | |
|---|---|
| Compound of Example 2 | 0.100 g |
| Polyethylene glycol (PEG 400) | 69.900 g |
| 95% ethanol | 30.000 g |

(e) Hydrophobic Ointment:

| | |
|---|---|
| Compound of Example 4 | 0.300 g |
| Isopropyl myristate | 36.400 g |
| Silicone oil ("Rhodorsil 47 V 300" marketed by Rhône-Poulenc) | 36.400 g |
| Beeswax | 13.600 g |
| Silicone oil ("Abil 300 000 cst" marketed by Goldschmidt) | qs 100 g |

(f) Nonionic Oil-in-water Cream:

| | |
|---|---|
| Compound of Example 5 | 1.000 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |

| | |
|---|---|
| Propyl para-hydroxybenzoate | 0.075 g |
| Sterile demineralized water | qs 100 g |

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound having the following structural formula (I):

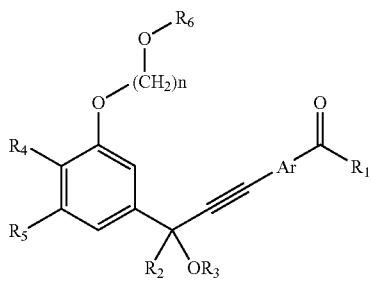

(I)

in which:

Ar is a radical of formulae (a) below:

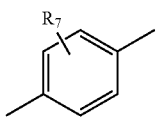

a)

wherein $R_7$ is as defined below;

$R_1$ is:
(a) a hydrogen atom,
(b) an alkyl radical having from 1 to 6 carbon atoms,
(c) a radical of formula:

(d) a radical —$OR_8$,
wherein R', R" and $R_8$ are as defined below;
$R_2$ is a hydrogen atom or an alkyl radical having from 1 to 6 carbon atoms;
$R_3$ is a hydrogen atom, an alkyl radical having from 1 to 6 carbon atoms or a radical —CO—$R_9$,
wherein $R_9$ is as defined below;
$R_4$ and $R_5$ together form, with the adjacent aromatic ring from which they depend, a 5- or 6-membered ring optionally substituted with methyl groups;
$R_6$ is an alkyl radical having from 1 to 6 carbon atoms or a radical —CO)$R_{10}$,
wherein $R_{10}$ is as defined below;
$R_7$ is a hydrogen atom, a halogen atom, an alkyl radical having from 1 to 6 carbon atoms or a radical —$OR_{11}$,
wherein $R_{11}$ is as defined below;
$R_8$ is a hydrogen atom, a linear or branched alkyl radical having from 1 to 20 carbon atoms, an alkenyl radical, a mono- or polyhydroxyalkyl radical, an optionally substituted aryl or aralkyl radical or a sugar residue or an amino acid or peptide residue;

$R_9$ and $R_{10}$ are each $CF_3$ or an alkyl radical having from 1 to 6 carbon atoms;
$R_{11}$ is H, an alkyl radical having from 1 to 6 carbon atoms or a radical —(CO)—$R_{12}$,
wherein $R_{12}$ is as defined below;
$R_{12}$ is an alkyl radical having from 1 to 6 carbon atoms;
R' and R" are each a hydrogen atom, an alkyl radical having from 1 to 6 carbon atoms, a mono- or polyhydroxyalkyl radical, an aryl radical or an amino acid, peptide or sugar residue;
n is an integer ranging from 2 to 6;
and the salts of the compounds of formula (I) when $R_1$ is a hydroxyl group, and also the optical and geometrical isomers of the compounds of formula (I).

2. An alkali metal or alkaline-earth metal, zinc or organic amine salt of the compound as defined by claim 1.

3. The compound as defined by claim 1, bearing at least one substituent selected from the group consisting of methyl, ethyl, n-propyl, isopropyl, cyclopropyl, n-butyl, i-butyl, t-butyl, n-pentyl and n-hexyl radicals.

4. The compound as defined by claim 1, bearing at least one substituent selected from the group consisting of methyl, ethyl, n-propyl, isopropyl, cyclopropyl, n-butyl, i-butyl, t-butyl, n-pentyl, n-hexyl, 2-ethylhexyl, octyl, dodecyl, hexadecyl and octadecyl radicals.

5. The compound as defined by claim 1, bearing at least one substituent selected from the group consisting of 2-hydroxyethyl, 2-hydroxypropyl and 3-hydroxypropyl radicals.

6. The compound as defined by claim 1, bearing at least one substituent selected from the group consisting of 2,3-dihydroxypropyl, 2,3,4-trihydroxybutyl and 2,3,4,5-tetrahydroxypentyl radicals, or a pentaerythritol residue.

7. The compound as defined by claim 1, bearing at least one substituent selected from the group consisting of a phenyl radical optionally substituted with at least one halogen, a hydroxyl or a nitro substituent.

8. The compound as defined by claim 1, bearing at least one substituent selected from the group consisting of benzyl and phenethyl radicals optionally substituted with at least one halogen, a hydroxyl group or a nitro substituent.

9. The compound as defined by claim 1, bearing at least one substituent selected from the group consisting of alkenyl radicals having from 2 to 5 carbon atoms and one or more sites of ethylenic unsaturation.

10. The compound as defined by claim 1, bearing at least one substituent selected from the group consisting of residues derived from glucose, galactose, mannose and glucuronic acid.

11. The compound as defined by claim 1, bearing at least one substituent selected from the group consisting of residues derived from lysine, glycine and aspartic acid.

12. The compound as defined by claim 1, bearing at least one substituent selected from the group consisting of dipeptide and tripeptide residues resulting from the combination of amino acids.

13. The compound as defined by claim 1, bearing at least one substituent selected from the group consisting of fluorine, chlorine and bromine atoms.

14. The compound as defined by claim 1, wherein at least one of the following conditions is satisfied:
n is 2 or 3,
$R_2$ is a hydrogen atom,
$R_4$ and $R_5$ form, with the adjacent aromatic ring, a 6-membered ring,
$R_6$ is an alkyl radical.

15. The compound as defined by claim 1, selected from the group consisting of:
4-{3-Hydroxy-3-[4-(2-methoxyethoxy)-5,5,8,8-tetramethyl-5,6,7,8-tetrahydronaphth-2-yl]prop-1-ynyl}benzoic acid;

4-{3-Hydroxy-3-[4-(2-ethoxyethoxy)-5,5,8,8-tetramethyl-5,6,7,8-tetrahydronaphth-2-yl]prop-1-ynyl}benzoic acid;

4-{3-Hydroxy-3-[4-(2-ethoxyethoxy)-5,5,8,8-tetramethyl-5,6,7,8-tetrahydronaphth-2-yl]prop-1-ynyl}-2-hydroxybenzoic acid;

4-{3-Hydroxy-3-[4-(2-ethoxyethoxy)-5,5,8,8-tetramethyl-5,6,7,8-tetrahydronaphth-2-yl]prop-1-ynyl}benzoic (S)-acid;

4-{3-Hydroxy-3-[4-(2-ethoxyethoxy)-5,5,8,8-tetramethyl-5,6,7,8-tetrahydronaphth-2-yl]prop-1-ynyl}benzoic (R)-acid;

4-{3-[4-(3-Ethoxyethoxy)-5,5,8,8-tetramethyl-5,6,7,8-tetrahydronaphth-2-yl]-3-hydroxyprop-1-ynyl}benzoic acid;

4-{3-[4-(3-Methoxypropoxy)-5,5,8,8-tetramethyl-5,6,7,8-tetrahydronaphth-2-yl]-3-hydroxyprop-1-ynyl}benzoic acid;

4-{3-[4-(4-Methoxybutoxy)-5,5,8,8-tetramethyl-5,6,7,8-tetrahydronaphth-2-yl]-3-hydroxyprop-1-ynyl}benzoic acid;

4-{3-[4-(5-Methoxypentoxy)-5,5,8,8-tetramethyl-5,6,7,8-tetrahydronaphth-2-yl]-3-hydroxyprop-1-ynyl}benzoic acid;

4-{3-[4-(6-Methoxyhexyloxy)-5,5,8,8-tetramethyl-5,6,7,8-tetrahydronaphth-2-yl]-3-hydroxyprop-1-ynyl}benzoic acid;

4-{3-[4-(2-Ethoxyethoxy)-5,5,8,8-tetramethyl-5,6,7,8-tetrahydronaphth-2-yl]-3-hydroxybut-1-ynyl}benzoic acid;

4-{3-[4-(2-Ethoxyethoxy)-5,5,8,8-tetramethyl-5,6,7,8-tetrahydronaphth-2-yl]-3-hydroxypent-1-ynyl}benzoic acid;

4-{3-[4-(2-Ethoxyethoxy)-5,5,8,8-tetramethyl-5,6,7,8-tetrahydronaphth-2-yl]-3-acetoxyprop-1-ynyl}benzoic acid;

4-{3-[4-(2-Acetoxyethoxy)-5,5,8,8-tetramethyl-5,6,7,8-tetrahydronaphth-2-yl]-3-hydroxyprop-1-ynyl}benzoic acid;

4-(3-Hydroxy-3-{5,5,8,8-tetramethyl-4-[2-(2,2,2-trifluoroacetoxy)ethoxy]-5,6,7,8-tetrahydronaphth-2-yl}prop-1-ynyl}benzoic acid;

4-(3-Hydroxy-3-[5,5,8,8-tetramethyl-4-(2-propionyloxyethoxy)-5,6,7,8-tetrahydronaphth-2-yl]prop-1-ynyl)benzoic acid;

2-Chloro-4-{3-[4-(ethoxyethoxy)-5,5,8,8-tetramethyl-5,6,7,8-tetrahydronaphth-2-yl]-3-hydroxyprop-1-ynyl}benzoic acid;

4-{3-[4-(2-Ethoxyethoxy)-5,5,8,8-tetramethyl-5,6,7,8-tetrahydronaphth-2-yl]-3-hydroxyprop-1-ynyl}-2-fluorobenzoic acid;

4-{3-[4-(2-Ethoxyethoxy)-5,5,8,8-tetramethyl-5,6,7,8-tetrahydronaphth-2-yl]-3-hydroxyprop-1-ynyl}-3-fluorobenzoic acid;

4-{3-[4-(2-Ethoxyethoxy)-5,5,8,8-tetramethyl-5,6,7,8-tetrahydronaphth-2-yl]-3-hydroxyprop-1-ynyl}-3-methylbenzoic acid;

Ethyl 4-{3-[4-(2-ethoxyethoxy)-5,5,8,8-tetramethyl-5,6,7,8-tetrahydronaphth-2-yl]-3-hydroxyprop-1-ynyl}benzoate;

Isopropyl 4-{3-[4-(2-ethoxyethoxy)-5,5,8,8-tetramethyl-5,6,7,8-tetrahydronaphth-2-yl]-3-hydroxyprop-1-ynyl}benzoate;

Isobutyl 4-{3-[4-(2-ethoxyethoxy)-5,5,8,8-tetramethyl-5,6,7,8-tetrahydronaphth-2-yl]-3-hydroxyprop-1-ynyl}benzoate;

2,3-Dihydroxypropyl 4-{3-[4-(2-ethoxyethoxy)-5,5,8,8-tetramethyl-5,6,7,8-tetrahydronaphth-2-yl]-3-hydroxyprop-1-ynyl}benzoate;

6-Glucosyl 4-{3-[4-(2-ethoxyethoxy)-5,5,8,8-tetramethyl-5,6,7,8-tetrahydronaphth-2-yl]-3-hydroxyprop-1-ynyl}benzoate;

6-Galactosyl 4-{3-[4-(2-ethoxyethoxy)-5,5,8,8-tetramethyl-5,6,7,8-tetrahydronaphth-2-yl]-3-hydroxyprop-1-ynyl}benzoate;

4-{3-[4-(2-Ethoxyethoxy)-5,5,8,8-tetramethyl-5,6,7,8-tetrahydronaphth-2-yl]-3-hydroxyprop-1-ynyl}-N,N-dimethylbenzamide;

4-{3-[4-(2-Ethoxyethoxy)-5,5,8,8-tetramethyl-5,6,7,8-tetrahydronaphth-2-yl]-3-hydroxyprop-1-ynyl}-N,N-diethylbenzamide;

(4-{3-[4-(2-Ethoxyethoxy)-5,5,8,8-tetramethyl-5,6,7,8-tetrahydronaphth-2-yl]-3-hydroxyprop-1-ynyl}-N-ethylbenzamide;

(4-{3-[4-(2-Ethoxyethoxy)-5,5,8,8-tetramethyl-5,6,7,8-tetrahydronaphth-2-yl]-3-hydroxyprop-1-ynyl}benzoylamino)acetic acid; and 2-(4-{3-[4-(2-Ethoxyethoxy)-5,5,8,8-tetramethyl-5,6,7,8-tetrahydronaphth-2-yl]-3-hydroxyprop-1-ynyl}benzoylamino)-3-phenylpropionic acid.

16. A pharmaceutical composition comprising a thus effective amounts of at least one ligand compound as defined by claim 1, formulated into a physiologically acceptable medium therefor.

17. The pharmaceutical composition as defined by claim 16, said at least one ligand compound comprising from 0.001% to 10% by weight thereof.

18. The pharmaceutical composition as defined by claim 16, said at least one ligand compound comprising from 0.01% to 1% by weight thereof.

* * * * *